(12) United States Patent
Pingel et al.

(10) Patent No.: US 6,509,967 B1
(45) Date of Patent: Jan. 21, 2003

(54) METHOD FOR DETECTING OPTICAL ERRORS IN LARGE SURFACE PANELS

(75) Inventors: Ulrich Pingel, Venusweg (DE); Christian Niepel, Erlenstrasse (DE)

(73) Assignee: Innomess Gelsellschaft fur Messtechnik mbH, Marl (DE)

( * ) Notice: Subject to any disclaimer, the term of this patent is extended or adjusted under 35 U.S.C. 154(b) by 0 days.

(21) Appl. No.: 09/284,437

(22) PCT Filed: Oct. 17, 1997

(86) PCT No.: PCT/EP97/05731
§ 371 (c)(1),
(2), (4) Date: Jul. 6, 1999

(87) PCT Pub. No.: WO98/17993
PCT Pub. Date: Apr. 30, 1998

(30) Foreign Application Priority Data

Oct. 18, 1996 (DE) .......................................... 196 43 107

(51) Int. Cl.⁷ ............................................... G01N 21/00
(52) U.S. Cl. .................................. 356/239.1; 356/239.7
(58) Field of Search .......................... 356/230.1, 239.2, 356/239.7, 237.2, 376; 250/562, 563, 572

(56) References Cited

U.S. PATENT DOCUMENTS

| | | | |
|---|---|---|---|
| 4,310,242 A | | 1/1982 | Genco et al. ................ 356/128 |
| 4,647,197 A | * | 3/1987 | Kitaya et al. ................ 356/239 |
| 5,128,550 A | * | 7/1992 | Erbeck ........................ 250/572 |
| 5,343,288 A | * | 8/1994 | Cohen et al. ................ 356/239 |

FOREIGN PATENT DOCUMENTS

| | | |
|---|---|---|
| EP | 0 416 302 A1 | 3/1991 |
| EP | 0 484 237 A1 | 10/1991 |
| EP | 0 559 524 A1 | 2/1993 |
| EP | 0 576 011 A1 | 6/1993 |
| EP | 0 416 302 B1 | 7/1993 |
| EP | 0 726 457 A2 | 2/1996 |

OTHER PUBLICATIONS

"Vision & Voice Magazine", by M. Selb and Dr. H. Höfler, vol. 4 (1990), No. 2, pp. 145–151.

* cited by examiner

*Primary Examiner*—Michael P. Stafira
(74) *Attorney, Agent, or Firm*—Nikolai & Mersereau, P.A.; C. G. Mersereau

(57) ABSTRACT

The invention relates to a method for detecting optical errors, especially in refractive power, in large surface panels made of transparent material such as glass, by evaluating an observed image. The steps of the inventive method include: projection of a defined model consisting of regular sequences, whereby the sequences includes two varying light intensities and arrangement of the panel in the optical path of projection. The inventive method enables detection of optical errors in at least one dimension of a panel without a reference screen by projecting the model onto a camera, whereby a model sequence is respectively represented on a certain number of adjacent camera pixels and the number is an integral multiple of the sequence.

24 Claims, 3 Drawing Sheets

METHOD FOR DETECTING OPTICAL ERRORS IN LARGE SURFACE PANELS

DESCRIPTION

1. Technical Field

The invention relates to a method for determining optical errors, in particular in the refractive power, in large-area panes composed of a transparent material such as glass, by evaluation of the observed image, comprising the steps of projecting of a pattern composed of regular sequences, with the sequences comprising at least two different light intensities, and arrangement of the pane in the beam path of the projection.

2. Prior Art

EP-A-0 416 302 describes such a method. In this method, an illuminated flat grid is imaged via an objective on a reference grid, a pane to be checked is arranged in the beam path between the flat grid and the reference grid, and the superimposed image composed of the image from the flat grid and the reference grid is investigated; in this case, the flat grid is imaged on a reference grid whose surface size is smaller than that of the pane to be examined, and the superimposed image is recorded a plurality of times by a video camera in order subsequently to be evaluated using a phase-shift method, in which the recorded brightness distribution is used as a measure of the refractive power of the pane.

An extremely high level of complexity is required to carry out this method. In practice, the flat grid is generally a cruciform grid which is formed from alternating opaque strips and transparent strips, with the transparent strips being exactly as wide as the opaque strips, and with two such strip patterns being superimposed offset through 90° with respect to one another. The pane to be examined is arranged in the beam path and is imaged on the reference grid, which is a linear grid, and likewise comprises transparent and opaque lines, to be precise with the same width ratio as the flat grid. A first practical problem arises when the lines of the two grids coincide exactly; in order to avoid this situation, lines which are semi-opaque and semi-permeable are in practice generally used as the flat grid rather than opaque lines. This reduces the contrast.

In order to allow evaluation of the resulting moiré image using the phase-shift method, the superimposed image of the flat grid which is imaged on the reference grid has to be imaged three times. In this case, the reference grid must be shifted twice, in each case by one third of the width of a line pair, so that, overall, at least three records are required in order to determine the phase shift in one dimension (for example the horizontal) of the pane. If it also desired to determine the refractive power of the pane in a dimension running at right angles to this (for example the vertical), three records of the resultant moiré image must be made once again, from a second reference grid. Thus, overall, six records are required in order to allow the refractive power of the pane to be determined using the phase-shift.

The apparatus for carrying out the method is correspondingly complex, since shifting the reference grid by one third of the width of a line pair on the reference grid must be carried out really precisely. The same is true for the second record, at right angles to the first, since it is difficult to avoid an undesirable moiré effect occurring due to positioning errors. A large amount of time is required to measure the refractive power, owing to the complex handling.

In addition, the known method can lead to undesirable moiré fringes on the "pixel period" of the camera (see column 4, lines 36–40) if the illumination pattern or the reference pattern make up a multiple of one period of the pixels. Measures therefore have to be taken to avoid the occurrence of this constellation, since these undesirable additional moiré images corrupt the evaluation of the image of the pane.

EP-A-0 559 524 describes another method, namely for testing the transparency in particular of laminated glass after the initial assembly process and before autoclaving, that is to say at a time at which the initial assembly, or the interlayer, as a rule has a milky color which impedes light transmission. This transmission method uses a light source arranged on one side (underneath) the initial assembly and a camera on the other side of the initial assembly in order to monitor the test image produced. The test image produced by the light source and projected is a line pattern comprising a small number of lines. A mean value from all the observed values is used as the basis for deciding whether a laminated glass pane is "good" or "poor". No specific imaging rule for the lines on the camera and its pixels is proposed. It is also impossible to detect errors in the refractive power, small inclusions or the like, since they have only a minimal effect on the measured mean value over the entire observed image.

The mathematical derivatives of angles originating from measured moiré images as well as a summary of the various moiré techniques are given in the article by Selb, M., and Höfler, H. in "Vision & Voice Magazine", Volume 4, (1990), No. 2, pages 145–151. This article also deals with high-resolution moiré topography measurements by gratings imaged directly onto a CCD chip, that is to say with single-stage imaging without a reference grating.

DESCRIPTION OF THE INVENTION

The object of the invention is to specify a method as claimed in the preamble of claim 1, using which optical errors in at least one dimension of a pane can be determined without a reference grid.

This object is achieved by the features in the descriptive steps of the claims, including imaging the pattern onto a camera, with a sequence of the pattern in each case being imaged onto a number of adjacently arranged pixels of the camera, and the number being an integer multiple of the sequence.

A sequence of the pattern can be defined by a periodic sequence of two or more light intensities. In the simplest case, this is a sequence in which light and dark strips, preferably of identical width, alternate with one another and form a light/dark sequence. However, it is also possible for the sequence to be composed of three, four or more strips, which have a regular sequence with intensity minima and maxima that are always equidistant.

In order to produce these sequences it is, on the one hand, possible to produce the light intensities by the local light permeabilities of a physical grid, by means of a light source arranged behind the grid. Where the grid is opaque, the light intensity is zero and the point is dark; where the grid is completely transparent, the light intensity assumes a maximum. The use of a physical grid as in the prior art, that is to say comparable to a large screen or filter, is adequate for sharp light/dark sequences. However, semi-transparent filters must be provided to produce sequences with strips of different brightness, which filters would possibly have to have three or more different light permeabilities, reproduced very precisely.

A light wall is preferably provided in an apparatus for carrying out the method, which light wall is used in the method according to the invention for projecting a pattern with regular sequences, and can be used instead of a light source with a grid. The light wall is expediently composed of a large number of individual LEDs which can be actuated as required individually, in blocks or in lines and columns in order either to illuminate or not to illuminate in accordance with a light/dark profile, or in order to emit different intensities as a function of a suitable characteristic. Similar light walls are used, for example, as display panels in sports stadiums. It is self-evident that the apparatus for determining optical errors, comprising a light wall composed of a plurality of light areas which can be actuated individually as a flat grid which is projected onto a pane whose refractive power is intended to be determined also works when it is used with a reference grid from the prior art. It is self-evident that, in principle, the light/dark sequence can be displayed with either or the two grids. It is furthermore self-evident that the sequences can also be enlarged via lenses, before the actual projection takes place.

If the number of adjacently arranged pixels according to the invention exceeds the total of two, it is self-evident that the pixels cannot all be arranged adjacent to one another in every situation; instead, the intention is that the pixels be arranged to be adjacent in pairs, in such a manner that they form a cohesive sub-line or sub-matrix which is free of unassociated pixels.

The method according to the invention preferably provides for an integer multiple, preferably a set of three pixels arranged alongside one another, to correspond to a light/dark sequence, preferably a light/dark pair, which is imaged by the pane onto the camera. The line pair width of the projected illumination pattern is thus precisely that multiple of the width of a pixel of the camera, so that moiré fringes are formed on the camera itself. The use of light/dark pairs has the advantage that the projection can be achieved very easily by the corresponding provision of a grid having only two different light permeabilities, expediently respectively opaque and transparent regions, so that good contrast is achieved.

This effect is used according to the invention to make it possible to dispense with a reference pattern, which, on its own, greatly simplifies the equipment required for an apparatus for carrying out the method, in particular the space required for the equipment.

It should be realized that there are a number of possible ways for evaluating the illumination pattern. On the one hand, the light intensity which is recorded by each pixel can be used as the basis for further processing. The precise width relationships allow periodically recurring intensity distributions to be produced, from whose disturbance the deflection angle causing the disturbance can easily be determined. A disturbance may be determined either by a comparison without a pane/with a pane or, if the initial points of the line pairs are aligned precisely with a set of three pixels, using the knowledge of the nominal light intensities at each point. In the latter case, it is preferably possible to dispense with a device with a test norm or the like.

Another approach to further processing of the lighting pattern, which is preferred owing to its very good resolution, is to use the moiré image that occurs on the pixels of the camera. The moiré image which is detected on the camera results from superimposition of two brightness distributions with a specific periodicity, in which case the approximate profiling of sinewave of the moiré structure can be recognized on the "grid" of pixels over the width of a line pair of the sequence which corresponds to a light/dark period. It is therefore possible to make use of the fact that moiré phenomena can be used to determine deformations in the pattern, for example resulting from refraction in the pane, with a resolution that is many times higher and is evident as a phase shift of the moiré image, that is to say as compression or expansion in the sinusoidal curve produced by the moiré image.

If, according to a first preferred development of the invention, a line pair of the lighting pattern is imaged on a set of three adjacent pixels, this thus results in 3 moiré image strips for each line pair; there is then no need to shift a reference pattern by one third with respect to the projected pattern and, instead of this, it is advantageously possible to use the value of the second and third pixels as the value for the record shifted through 120° and 240° (or −120°). These moiré image strips, offset through 120° (one third of a complete sine wave) and detected by the pixels of the camera can, after simple conversion, be expressed mathematically as curves that are dependent on a sine function.

Variations in the refractive power of the panes, for example a windshield of a motor vehicle, lead to variations in the maxima and minima which occur as a result of the moiré phenomenon and can easily be determined as a phase shift in the sine wave; if the distance between the camera and the pane is known, this can be used to determine the angle through which the light that passes through the pane is refracted. The refractive power in dioptrins can thus be determined by simple further mathematical processing (differentiation). This is of major importance, particularly for determining the refractive power of a windshield, since deflection of the view in the vertical plane has an adverse effect on the view straight ahead, while deflection of the light in the horizontal plane has an adverse effect on the view to the side. DIN 52305 and ECE 43 quote limits for the maximum permissible refractive power of the glass, and these can be used as threshold values for a comparison as to whether a tested windshield is accepted or rejected.

If the method according to the invention makes use of a pattern which arranges sequences superimposed on one another both in the horizontal plane and in the vertical plane, then a matrix camera can be used to carry out a simultaneous evaluation of the refractive power both for the vertical plane and for the horizontal plane, without the camera or a reference grid having to be rotated for this purpose. The same measured values of the pixels of the camera can be used as the basis of the evaluation, which results in a large amount of memory space being saved for each evaluation, and the measurement data can be archived in a compact form. If the number of pixels associated with a light/dark pair is increased, by a factor of, for example, four (five) or more, this allows an evaluation to be carried out using a phase-shift method shifted in each case by 90° (72°) or corresponding fractions of these figures. In the case of four pixels, the additional degree of freedom which becomes available also allows the frequency shift to be determined easily, in addition to the position and intensity extremes.

According to a second preferred development of the invention, it is possible to achieve the same resolution as for a set of three pixels by imaging on only two respectively adjacent pixels in the camera. The pattern that needs to be provided for this purpose is only slightly more complex.

In a first variant, it is possible to form a pattern with sequences composed of three light intensities, in which case this sequence can be formed, for example, as three equidistant strips of a grid. The light permeabilities of the grid may each differ by a factor as, for example, 1%, 10%, 100%, or 10% as well as 0%, 30% as well as 33%, 90% as well as 100%. The signal detected by the two pixels can then likewise lead back to a sine wave, which allows subsequent evaluation using phase-shift methods. Alternatively, the light intensities are prod ed by fields of a light matrix whose lighting intensities differ in lines and/or columns.

In another variant, it is possible to provide at least one "strip which can be switched off" which is transparent, for example, only for light at a specific wavelength (of a specific color) in each sequence of the grid. By alternately illuminating firstly with light passing through and secondly with absorbed light, the size ratio of the light/dark sequence is varied in a defined manner while maintaining its "grid constant" that is relevant for the moiré phenomenon, by which means phase shifts in the moiré image can be evaluated very easily. For example, the grid for producing the light/dark sequence is composed of strips which are all of the same width and are alternately completely opaque, transparent for red light but not for green, and completely transparent. It is possible first of all to make one record each with illumination using red or green light, and then to use both images as the basis for the evaluation. It is easier to illuminate alternately with red and green in a rapid frequency sequence, as a result of which the "strip which can be switched off" appears respectively light and dark. Phase evaluation using a modified phase-shift method can be carried out by integration of the light intensity in the pixel (which detects only light/dark, that is to say is independent of the color of the light).

A third advantageous development of the invention is for at least three adjacent strips (lines or columns) of the grid pattern (which then form a sequence) to be illuminated in each case successively, with a corresponding number of records, that is to say at least three, being made of the pane, and each sequence being imaged on a pixel (or on an integer multiple of this) . This development can be carried out both with illumination, as already described above, of a grid having light permeabilities which are dependent on the light color, and with a physical filter, which is in each case shifted by the width of one strip (it is self-evident that the strips are then at equidistant intervals). Light walls such as those described above can be used particularly advantageously and ensure a rapid sequence of the three records with a position which is always reproducible at the same time. Furthermore, this light wall can also be used to make records of the horizontal refractive power immediately after those for the vertical refractive power. This development has the advantage that, on the one hand, it is possible to continue to use existing evaluation software while, on the other hand, only a relatively small number of camera pixels are required, so that it can be carried out cheaply. A matrix light panel also allows, for example, the exposure time of the camera and the duration of the illumination in the grid to be synchronized for a number of, for example, mutually inverse, records. If a pane is scanned using a line-scan camera, each sequence can then be illuminated once for each scanned line, as a result of which it is possible to evaluate each recorded sequence virtually on-line, and the camera need be moved or pivoted only once to scan the pane.

According to a further preferred development of the invention, it is possible, on the basis of the method explained above, to design an apparatus for determining the refractive power in car window panes, in particular windshields, in such a manner that the grid has, for example, a pattern with a strip sequence composed of red, green and blue in the otherwise transparent material, so that the corresponding light color does not pass through the respective strip, and a camera records this strip as "dark". A color camera thus allows a light/dark strip pattern (one sequence for two adjacent pixels in each case) shifted by one third to be recorded for each of the three colors directly, and the resultant moiré image to be evaluated later. It is self-evident that the sequence of the three colors is then imaged on at least one pixel in the camera, or on a multiple thereof. Alternatively, it is also possible then to illuminate the grid alternately, for example by means of LEDs, with the three corresponding colors, so that the respectively corresponding strip appears dark, and the two other strips appear light. If a black-and-white line-scan or matrix camera is used, it is then expedient to base the evaluation to determine a phase on more than one record with the camera.

The methods according to the invention allow the desired refractive power indices to be determined very precisely and very quickly and are thus particularly suitable for use on motor vehicle panes composed of prestressed glass or of laminated safety glass as well as for flat glass manufactured in the form of float glass, drawn glass or rolled glass, acrylic glass or PVC, LCD displays etc. However, it is also possible to use the methods according to the invention to investigate the refractive power of other transparent materials as may be used, in particular, for vision aids composed of glass or plastics and for large telescope mirrors, for transparent canopies in aircraft or motor cycle helmets etc.

Further refinements of the invention can be found in the following description and the dependent claims.

The invention is explained in more detail in the following text with reference to outline sketches which are illustrated in the attached figures.

DESCRIPTION OF PREFERRED EXEMPLARY EMBODIMENTS

Figure 1:
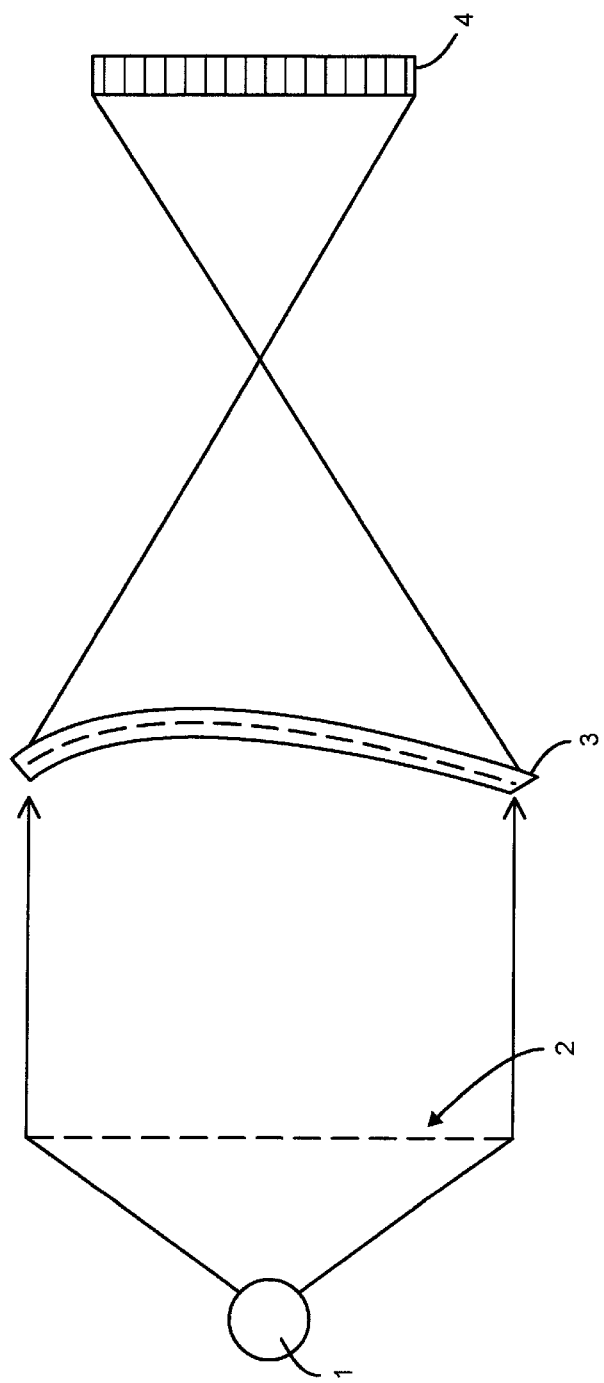
FIG. 1 shows schematically the beam path of an apparatus for carrying out the method according to the invention.

Referring now to FIG. 1, a light source 1 can be seen which illuminates an illuminated grid 2 which is designed as a cruciform grid and from which parallel light strikes the windshield 3 arranged in the beam path. It is self-evident that, instead of the windshield 3, it is also possible to measure any other object which is transparent at least for light at specific wavelengths, preferably in the visible band.

Figure 2:
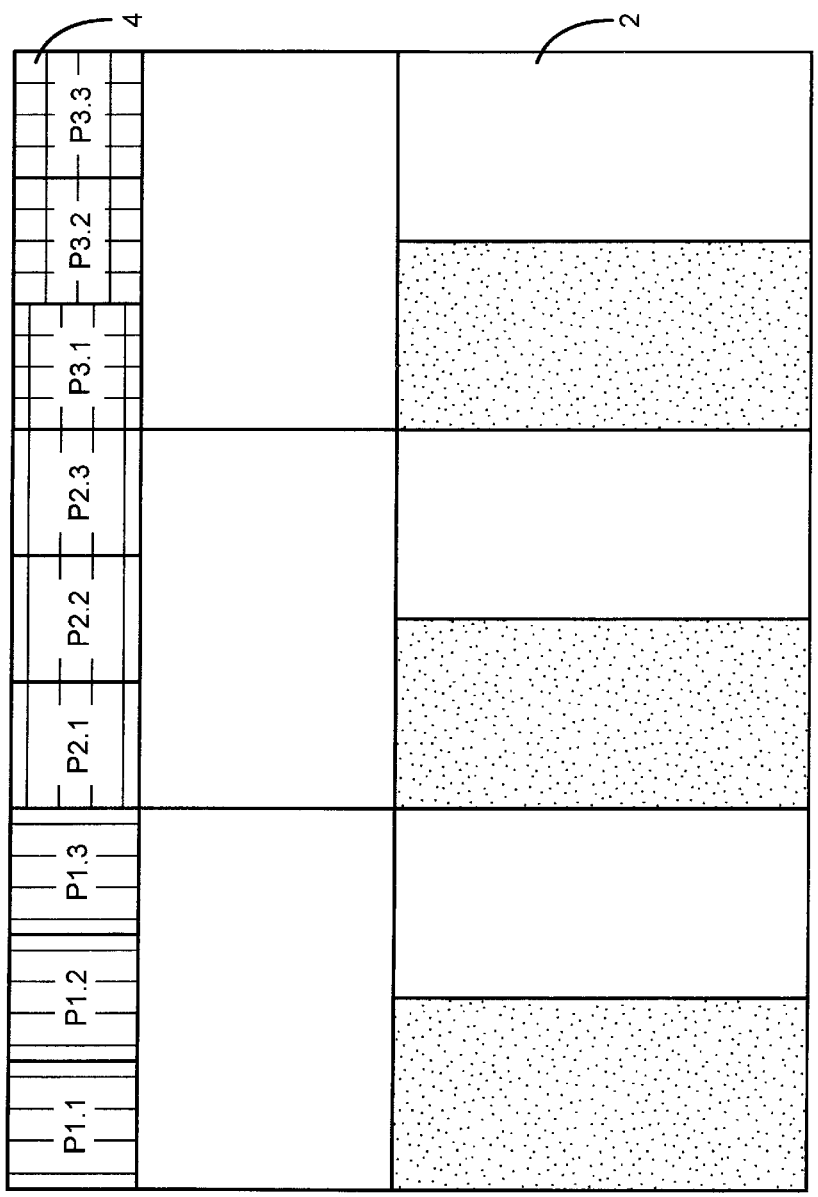
FIG. 2 and FIG. 3 show the relationship between sequences of a lighting pattern and camera pixels for a single-dimensional and a two-dimensional method, respectively.
Figure 3:
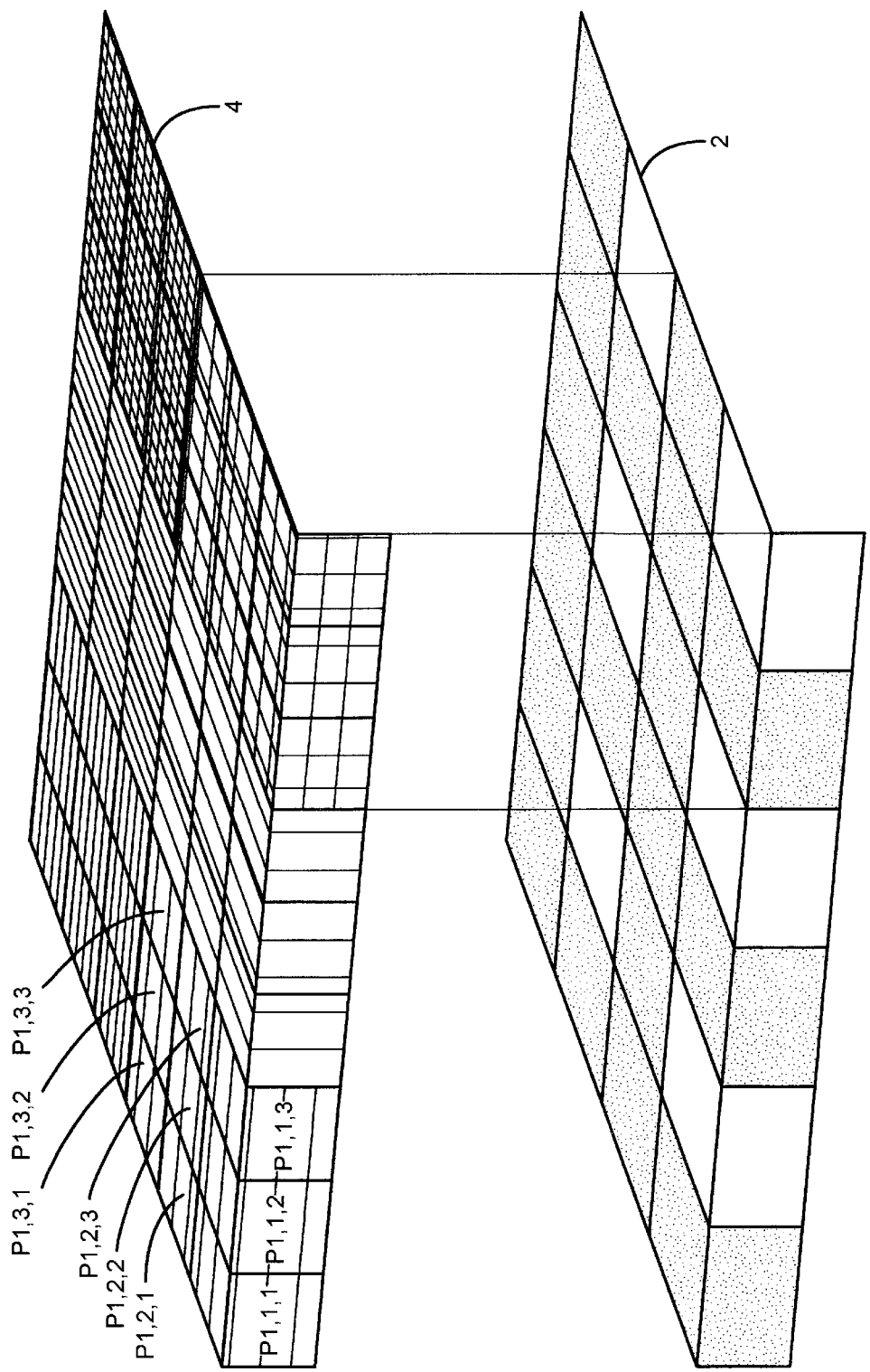

The cruciform grid 2 splits the light arriving from the light source 1 in such a manner that only a quarter of the light passes through, while the remaining three quarters of the light is prevented from passing through by horizontal opaque strips and vertical opaque strips which cross one another and bound the transparent squares. The edge length of the transparent squares and of the opaque strips is identical. This results in the light/dark pattern as can be seen in FIGS. 2 and 3.

The dimensions of the grid 2 correspond roughly to the size of the object to be measured.

The grid 2 is imaged through the windshield 3 directly and without the interposition of a reference grid on a camera 4, which records the light/dark intervals on the windshield. It is self-evident that, instead of opaque and transparent lines, it is also in general possible to use lines of different transparency, possibly also with respect to just one specific frequency spectrum, to which the camera 4 is sensitive.

In the case of an "ideal" windshield, the image of the cruciform grid 2 would be projected onto the camera without being changed. The cruciform grid 2 and the camera 4 are matched to one another in such a manner that one pair of light/dark strips is in each case imaged onto three adjacent pixels in the camera 4, as can be seen more clearly in FIGS. 2. and 3. Based on the individual pixels, which are denoted $P_{i,j}$ (FIG. 2) and $P_{i,j,k}$ (FIG. 3), where i is the i-th strip pair in the cruciform grid (and the i-th set of three pixels), j is the j-th pixel (j=1, 2 or 3) in the set of three in the direction of the strip and, in the case of a matrix camera, k is the k-th pixel (k=1, 2 or 3) at right angles to the extent of the j-th pixel for in each case one line in the matrix of pixels; it is self-evident that a line index also exists. These pixel addresses can also be addressed individually in the subsequent evaluation of the matrix.

In the case of an ideal image on the camera 4, the fact that the grid frequency of the camera pixels and the grid frequency of the illuminated grid 2 are multiples of one another leads to a regular moiré phenomenon, which is registered at the camera. Phase shifts as well as expansions and compressions of the sine wave can be determined simply by converting the values measured by the pixels into a sine-wave function.

If, owing to light refraction in the pane, the image on the camera 4 is no longer ideal, but has discrepancies, the moiré phenomenon is disturbed at the camera pixels and can be detected as a phase shift at the output of the camera pixels, thus allowing the angle through which the light beam has been deflected to be determined, with little effort. Based on this angle, it is possible by differentiation to determine the refractive power of the windshield in the vertical direction, which influences the view straight ahead, and in the horizontal direction, which influences the view to the side.

By choosing the ratio of one grid line pair (that is to say 2 lines, one bright and one dark) to 3 pixels, this allows a very good ratio of the width dimensions to one another, as a result of which the resolution of the measured values becomes very high, and the maximum permissible size of the windshield 3 which can be measured becomes very large. The equipment complexity for the apparatus remains low.

It is self-evident that, instead of light/dark pairs or of the cruciform grid 2, grids with a plurality of brightness steps can be used in a comparable manner by sequences with more than two light intensities. The number of pixels per light/dark pair or sequence may also be four, five, . . . in a corresponding manner.

It is furthermore self-evident that, instead of the arrangement having a light source 1 and a grid 2, a panel corresponding to the size of the grid and having an LED matrix could also be used, which would advantageously make it possible to drive the individual LED strips via specific electrical contacts. Other means for producing a light pattern may also be used instead of an illuminated grid. The grid has the advantage that simple geometric shapes such as lines can be produced cheaply even if the precision requirements are stringent.

What is claimed is:

1. A method for determining optical errors, in particular in the refractive power, in large-area panes composed of a transparent material such as glass, by evaluation of an observed image, comprising the steps:
   (a) Aiming of a defined pattern composed of regular sequences of a light intensity and a dark intensity towards a camera, thus defining a beam path;
   (b) arranging the pane in the beam path of the pattern;
   (c) imaging of the pattern beyond the pane on the camera; and
   (d) arranging the pattern such that each observed sequence of the pattern is exactly imaged on an integer number of adjacent pixels of the camera, wherein said integer number is selected from the group of integer numbers consisting of two, three, four and five.

2. A method for determining optical errors, in particular in the refractive power in large-area panes composed of a transparent material such as glass, by evaluation of an observed image, comprising the steps:
   (a) aiming of a defined pattern composed of regular sequences towards a camera, thus defining a beam path, with the sequences comprising at least two different light intensities;
   (b) arranging of the pane in the beam path of the pattern;
   (c) imaging of the pattern beyond the pane on the camera with a sequence of the pattern in each case being imaged on a number of adjacently arranged pixels in the camera, said number being an integer multiple of said sequence;
   (d) wherein a record for the evaluation of a moiré image is based on the pixels of the camera.

3. The method as claimed in claim 2 wherein the sequence of the pattern comprises at least two light intensities, and wherein the integer multiple is at least three.

4. The method as claimed in claim 2 wherein a grid is provided for producing the pattern and wherein the grid comprises equidistant opaque and transparent strips in order to produce a regular light/dark pattern.

5. The method as claimed in claim 2 wherein a grid is provided for producing the pattern and wherein the grid comprises transparent squares which are bounded by opaque lines having the same width as the squares, so that essentially one quarter of the grid is transparent and wherein the camera is one of a line-scan camera and a matrix camera.

6. The method as claimed in claim 5 wherein a two-dimensional sequence of the pattern comprises a transparent square and two crossing opaque lines, with the surface area of the crossing lines being coincident with the transparent square.

7. The method as claimed in claim 6 wherein the two-dimensional sequence is imaged on respectively adjacent n×n pixels of a matrix camera, where n is an integer multiple of the sequence greater than two.

8. The method as claimed in claim 2 wherein a grid is provided for producing the pattern and wherein the grid is formed as a checkerboard pattern composed of opaque and transparent congruent squares and wherein the camera is one selected from the group consisting of line-scan cameras and matrix cameras.

9. The method as claimed in claim 8 wherein a square surface area comprising two pairs of light and dark squares, which are arranged diagonally offset with one another, are imaged on respectively adjacent n×n pixels of a matrix camera, where n is an integer greater than two.

10. The method as claimed in claim 2 wherein a sequence comprises at least three different light intensities, wherein the integer multiple is at least two and wherein the camera is one selected from the group consisting of line-scan cameras and matrix cameras.

11. The method as claimed in claim 2 wherein a grid is provided for producing the pattern and wherein the grid comprises a strip pattern of different light permeabilities.

12. The method as claimed in claim 11 wherein the grid comprises a second strip pattern of different light permeabilities at right angles to the strip pattern so that the superimposition of the strip patterns produces a pattern of rectangles of different light permeabilities, with at least three different light permeabilities overall.

13. The method according to claim 10 wherein two records for the evaluation of a moiré image are based on the pixels of the camera.

14. The method as claimed in claim 2 wherein the pattern comprises a large number of strips which can be actuated selectively in such a manner that each strip appears either light and dark, wherein each n-th strip in the sequence is illuminated at the same time, where n is at least equal to three and wherein n adjacent strips are imaged successively on exactly an integer multiple of one pixel of the camera.

15. The method as claimed in claim 2 wherein the camera is one selected from the group consisting of line-scan cameras and matrix cameras which is displaced in order to scan a plurality of sequences.

16. The method as claimed in claim 2 comprising an evaluation step in which a change in the refractive power with respect to an illumination pattern in the pane is determined at the corresponding point on the basis of a phase shift which occurs on the pixels of the camera.

17. The method as claimed in claim 16 wherein the evaluation step comprises the formation of a difference in the phase profile of the image with a light-refracting pane to a state without light refraction.

18. The method as claimed in claim 16 wherein the refractive power is determined by the differentiation of the angle through which the light beam is deflected in the pane.

19. The method as claimed in claim 2 wherein the pane is one of curved glass and plastic.

20. The method as claimed in claim 2 wherein the camera is a color camera and wherein the evaluation of the same image is carried out with respect to the different recorded colors.

21. A method for determining optical errors, in particular in the refractive power in large-area panes composed of a transparent material such as glass, by evaluation of an observed image, comprising the steps:
  (a) aiming of a defined pattern composed of regular sequences towards a camera, thus defining a beam path, with the sequences comprising at least two different light intensities;
  (b) arranging of the pane in the beam path of the pattern; and
  (c) imaging of the pattern beyond the pane on the camera, with a sequence of the pattern in each case being imaged on a number of adjacently arranged pixels in the camera;
  wherein a grid comprising a strip pattern of different light permeabilities is provided for producing the pattern; and wherein the light permeability of the grid varies as a function of the wavelength of the light.

22. A method for determining optical errors, in particular in the refractive power in large-area panes composed of a transparent material such as glass, by evaluation of an observed image, comprising the steps:
  (a) aiming of a defined pattern composed of regular sequences towards a camera, thus defining a beam path, with the sequences comprising at least two different light intensities;
  (b) arranging of the pane in the beam path of the pattern;
  (c) imaging of the pattern beyond the pane on the camera, with a sequence of the pattern in each case being imaged on a number of adjacently arranged pixels in the camera; and
  (d) selectively actuating lines and columns of a matrix of LEDs, wherein a projection of the LEDs is aimed directly to the pane.

23. The method according to claim 22, wherein the LEDs of the matrix are actuated to define on pattern selected from the group consisting of strips and checkerboard.

24. A method for determining the refractive power in large-area panes composed of a transparent material such as glass, by evaluation of an observed image, comprising the steps:
  (a) aiming of a defined pattern composed of regular sequences towards a camera selected from the group consisting of line-scan cameras and matrix cameras, thus defining a beam path, each sequence comprising at least two different light intensities;
  (b) arranging of the pane in the beam path of the pattern;
  (c) imaging of the pattern beyond the pane on the camera;
  (d) recording the pattern with the camera; and
  (e) evaluating variations in a Moire image generated by said defined pattern and on the pixels of the camera for determining local distortion angles in the pane.

\* \* \* \* \*